United States Patent [19]

Petrofsky et al.

[11] Patent Number: 4,499,900
[45] Date of Patent: Feb. 19, 1985

[54] SYSTEM AND METHOD FOR TREATING PARALYZED PERSONS

[75] Inventors: Jerrold S. Petrofsky, Beavercreek; Chandler A. Phillips, Tipp City; Roger M. Glaser, Dayton; Harry H. Heaton, III, Beavercreek, all of Ohio

[73] Assignee: Wright State University, Dayton, Ohio

[21] Appl. No.: 444,647

[22] Filed: Nov. 26, 1982

[51] Int. Cl.³ .............................................. A61N 1/36
[52] U.S. Cl. .............................................. 128/423 W
[58] Field of Search ..... 272/73, 129, DIG. 4–DIG. 6; 128/421–423, 677, 707, 796

[56] References Cited

U.S. PATENT DOCUMENTS

| | | | |
|---|---|---|---|
| 1,498,529 | 6/1924 | Allen | 128/796 |
| 3,236,240 | 2/1966 | Bradley | 128/421 |
| 3,387,147 | 4/1967 | Radwan | 307/275 |
| 3,395,698 | 8/1968 | Morehouse | 128/707 |
| 3,730,174 | 8/1973 | Madison | 128/25 |
| 3,817,254 | 3/1974 | Maurer | 128/421 |
| 3,845,756 | 11/1974 | Olsson | 128/707 |
| 3,911,910 | 9/1975 | Oesau | 128/82.1 |
| 3,930,495 | 2/1976 | Marino, Jr. | 128/25 |
| 3,989,240 | 6/1976 | Victor et al. | 272/125 |
| 4,147,171 | 4/1979 | Greene et al. | 128/421 |
| 4,177,819 | 10/1979 | Kofsky et al. | 128/422 |
| 4,235,437 | 11/1980 | Ruis et al. | 272/129 |
| 4,244,021 | 1/1981 | Chiles | 272/73 |
| 4,284,157 | 4/1981 | Lay | 180/65 |
| 4,378,807 | 4/1983 | Peterson et al. | 128/677 |
| 4,392,496 | 7/1983 | Stenten | 128/423 W |
| 4,402,502 | 9/1983 | Peters | 272/73 |
| 4,408,613 | 10/1983 | Relyea | 128/670 |
| 4,423,863 | 1/1984 | Figueroa | 272/73 |

OTHER PUBLICATIONS

Strojnik et al., "Programmed Six-Channel Electrical Stimulator for Complex Stimulation of Leg Muscles During Walking", *IEEE Trans. Biomeg. Eng.*, vol. BME-26, No. 2, Feb. 1979, pp. 112–116.
Petrofsky, "Sequential Motor Unit Stimulation through Peripheral Motor Nerves in the Cat", *Med. & Biol. Eng. & Comp.*, Jan. 1979, vol. 17, pp. 87–93.
Jacobsen et al., "An Ergometer Controlled by Heart Rate", *Med. & Biol. Eng.*, Sep. 1974, pp. 675–680.
Microprocessor Controlled Stimulation in Paralyzed Muscle, Petrofsky & Phillips, IEEE NAECON Record (1979), pp. 198–210.
New Microcomputer May Someday Bring Paralyzed Limbs to Life, The Washington Post, Feb. 16, 1961 by Philip J. Hilts.
Control of Contraction Strength of Electrically Stimulated Muscle by Pulse Width and Frequency Modulation, Peckham, Proc. 29th ACEMB, p. 116, Nov. 6–10, 1976.
Walking Away from Paralysis by Denise Grady, Discover Magazine, May 1981, pp. 26–28 and 30.

*Primary Examiner*—William E. Kamm
*Assistant Examiner*—Mitchell J. Shein
*Attorney, Agent, or Firm*—Biebel, French & Nauman

[57] ABSTRACT

Apparatus and method for therapeutic treatment of persons having paralyzed legs. The apparatus and method make use of four sets of transcutaneous electrodes which are placed above the iliac and quadriceps muscles of the paralyzed person. The person is seated upon an exercycle, and a series of pulsed stimulation signals are applied to the electrodes to cause coordinated contraction of the iliac and quadriceps muscles. This causes pedaling of the exercycle by the paralyzed legs. A position sensor senses the position of the pedals and transmits an indication thereof to a computer which generates control signals for stimulation driving circuits connected to the stimulation electrodes. A pair of paddle controllers are connected to the computer for manual adjustment of the stimulation amplitude.

35 Claims, 7 Drawing Figures

SYSTEM AND METHOD FOR TREATING PARALYZED PERSONS

CROSS-REFERENCE TO RELATED APPLICATIONS

This application is related to Petrofsky et al Ser. No. 417,934, Petrofsky et al Ser. No. 417,935, Petrofsky et al Ser. No. 417,938 and Glaser et al Ser. No. 517,933, all of which applications were filed Sept. 14, 1982.

BACKGROUND OF THE INVENTION

The present invention relates to a method and apparatus for treating paralyzed persons, and more particularly, a computer controlled method and apparatus for stimulating the muscles of a paralyzed person to operate an exercycle or the like. Paralyzed individuals frequently suffer from seemingly unrelated health problems that arise as a consequence of their paralysis. For example, in the case of paraplegics, decreased physical activity due to non-use of the muscles of the lower body can often lead to various problems such as poor circulation, cardiovascular disease, and a loss of calcium from the bones, which then become vulnerable to fractures.

The invention which is disclosed and claimed herein has particular value in the treatment of persons who have suffered injuries resulting in spinal cord damage. This particular type of damage often times produces partial or total paralysis of muscles which are controlled from a point below the point of spinal cord damage. It is well known that the muscles themselves are undamaged and that atrophy can be avoided by a program of exercise. Prior art treatment of paraplegics and quadriplegics has therefore commonly employed manual manipulation of the legs, as well as massaging and use of mechanical vibrators. More recently the treatment has involved use of motor-driven devices for automatic manipulation, as taught for instance in Madison U.S. Pat. No. 373,174 and in Marino U.S. Pat. No. 3,930,495.

It will be appreciated that the prior art techniques are merely "passive" in nature and do not exercise the muscles in the true sense. That is, the muscles are moved, but they are not caused to do any work. Thus while atrophy is avoided, muscle tone is not maintained, and the cardiovascular system is not exercised.

SUMMARY OF THE INVENTION

In accordance with this invention a method and apparatus are provided whereby the legs of a paralyzed person are stimulated to work against a load by pedaling an exercycle of conventional design. The paralyzed person is seated in the conventional manner, and his feet are attached to the pedals of the exercycle. Sets of stimulation electrodes are attached to the skin of the person for stimulation of the left and right iliac and quadriceps muscles. The legs are started in motion either manually or through use of a motor-drive, and then stimulation is commenced. Stimulation is carried out by applying a series of alternately pulsed voltages to the stimulation electrodes. This produces coordinated movement of the legs whereby pedaling of the exercycle is performed by the paralyzed person himself.

Pedaling is under control of a sensing system and a computer which sense the pedal position and adjust the stimulation signals accordingly. The system divides the pedal position angle into four quadrants with the right pedal as the reference. The first quadrant begins with the top dead center position of the pedal and continues for 90°. The second, third and fourth quadrants are succeeding 90° sectors in the clockwise direction. During the first quadrant the left iliac and right quadriceps muscles are stimulated. During the second quadrant stimulation is applied only to the left iliac muscle. During the third quadrant the right iliac and left quadriceps muscles are stimulated, while during the fourth quadrant only the right iliac is stimulated.

In a physical therapy method according to this invention, electrical stimulation signals are applied to the iliac and quadriceps muscles of a paralyzed person to produce coordinated movement of the legs. The movement of the legs is impeded to cause a power output from the legs, the power output is measured, and the stimulation signals are adjusted to maintain the power output at a predetermined level. Further in accordance with this invention, it has been found that the blood pressure of the exercising paralyzed person provides a reliable indication of physical stress, whereas the pulse rate measurement, commonly used for normal persons, does not.

It is therefore an object of this invention to provide apparatus and method for therapeutic treatment of the legs and the cardiovascular system of a paralyzed person.

It is another object of this invention to provide a system whereby a paralyzed person can engage in a program of coordinated leg exercise under the power of his own muscles.

It is yet another object of the invention to provide a system whereby a paralyzed person may be enabled to operate an exercycle.

Other objects and advantages of the present invention will be apparent from the following description, the accompanying drawings, and the appended claims.

DESCRIPTION OF THE PREFERRED EMBODIMENT

Figure 1:
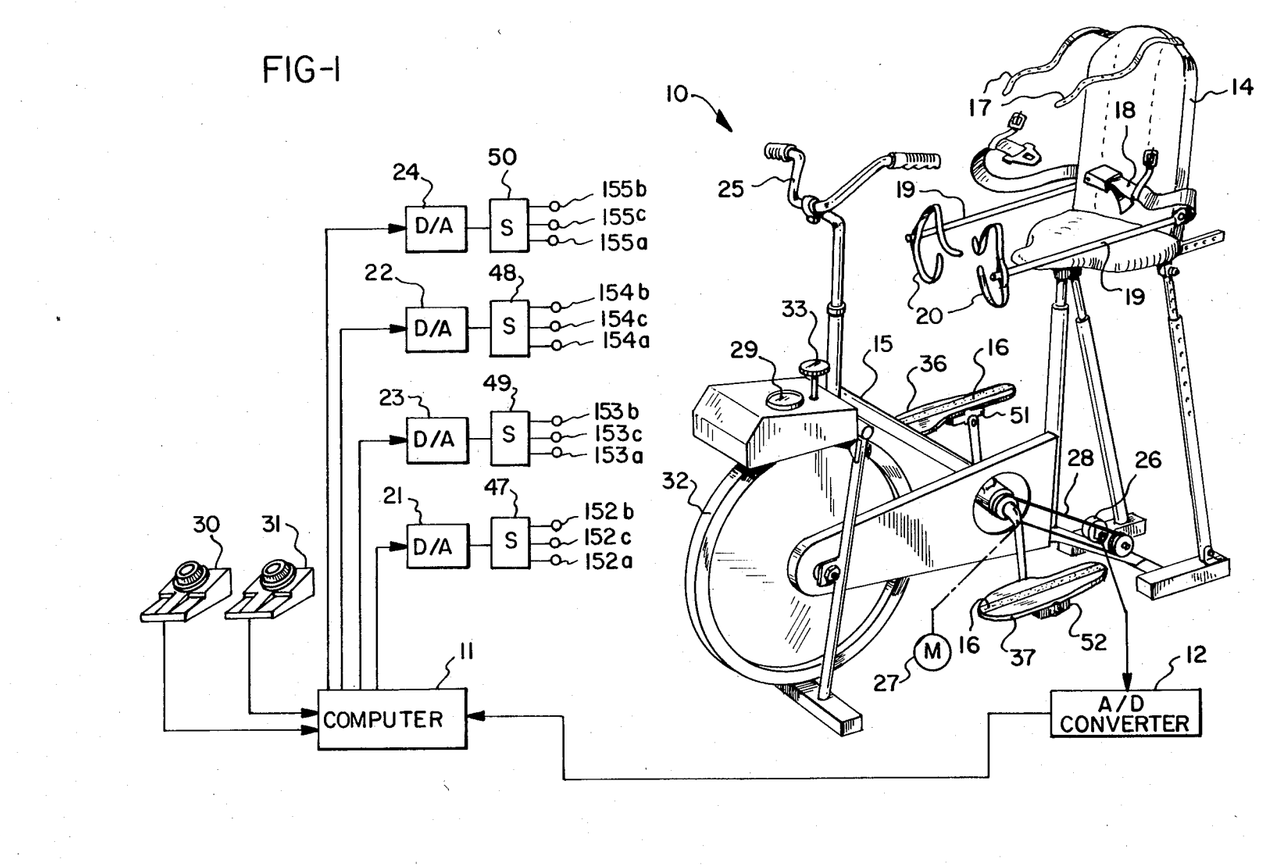
FIG. 1 is a schematic diagram of a treatment system according to the present invention.

A treatment system in accordance with the present invention may be arranged as generally illustrated in FIG. 1. Accordingly, the system may comprise an exercycle 10, a computer 11, an analog to digital converter 12, four digital to analog converters 21 through 24 and four stimulation drivers 47 through 50. Stimulation drivers 47 through 50 provide stimulation signals for a set of twelve stimulation electrodes 152a through 152c, 153a through 153c, 154a through 154c and 155a through 155c. Computer 11 is preferably an Apple II Plus computer sold by Apple Computer Inc. of Cupertino, Calif.

Computer 11 is used with two paddle controllers 30 and 31, the operation of which will be described hereinafter.

Figure 2:
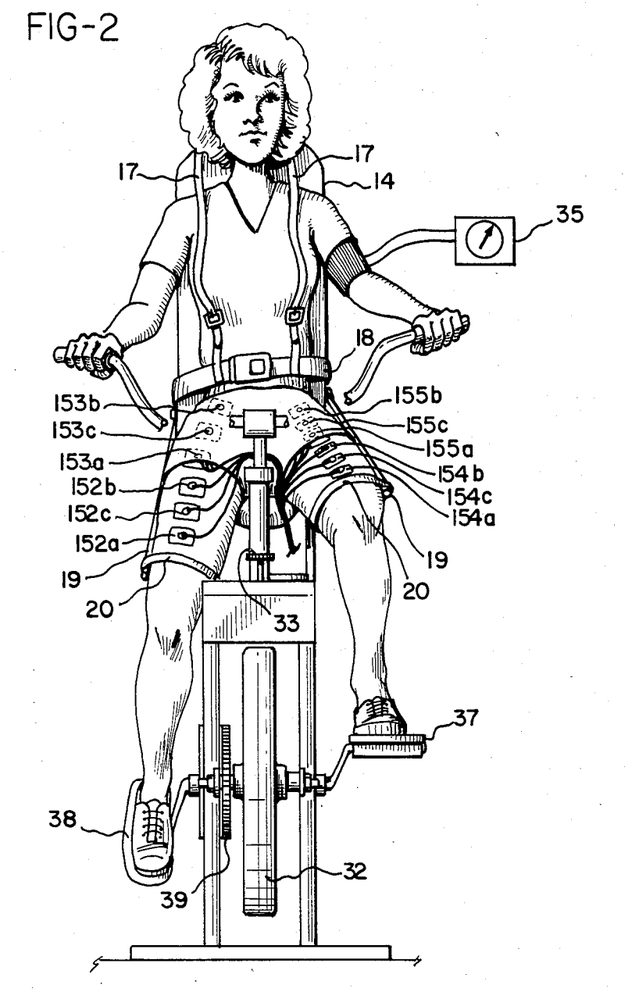
FIG. 2 illustrates the operation of an exercycle by a paralyzed person.

Exercycle 10 may be of conventional design, except for modifications as hereinafter described. Accordingly, exercycle 10 comprises a frame 15 upon which are mounted handlebars 25, a pair of pedals 51 and 52 and a flywheel 32. The paralyzed operator is seated on a chair 14 provided with a seatbelt 18, shoulder straps 17, 17 and a pair of leg braces 19, 19. Leg braces 19, 19 are attached to the legs of the operator by a pair of straps 20, 20 as illustrated in FIG. 2. If necessary, the operator may wear shoes which provide extra ankle support.

A pair of foot plates 36, 37 are mounted upon pedals 51, 52 respectively for receiving the feet of the operator. Foot plates 36, 37 are provided with strips of hook and loop fabric 16 for engagement with similar fabric secured to the soles of the operator's shoes. Such fabric is widely available under the trademark VELCRO. Strips 16 insure engagement of the operator's feet with foot plates 36, 37 throughout the course of a therapy procedure, while providing a break-away feature for the safety of the operation.

Exercycle 10 also comprises a speed indicator 29 and a tension control knob 33, both of which may be of conventional design. Tension control 33 controls the operation of a brake 38 (see FIG. 3) which may be of any conventional type. Since exercycle 10 is stationary, the reading on indicator 29 is merely the circumferential speed of flywheel 32. It will be appreciated that the speed indication on indicator 29 is also an indirect indication of the power output from the legs of the operator.

FIG. 2 illustrates the operation of exercycle 10 by a paralyzed person. The person is seated on seat 14 with seatbelt 18 and shoulder straps 17, 17 engaged. Her feet are placed in engagement with foot plates 37 and 38, and leg braces 19, 19 are attached to her legs. Braces 19, 19 provide a damping force to keep the legs from moving sidewardly in and out during a therapy procedure. For the normal, healthy individual slight muscle activity prevents such leg movement, but for a paralyzed person some sideward support has been found to be desirable.

The twelve stimulation electrodes are attached to the skin of the person in a pattern as generally illustrated in FIG. 2. The electrodes are transcutaneous stimulation electrodes and may be of the type sold under the trademark MEDTRONIC by Medtronic, Inc. of Minneapolis, Minn. Electrodes 152a through 152c are placed in a pattern over the right quadriceps muscles. These electrodes may be MEDTRONIC Model 3793 electrodes. Electrodes 153a through 153c may be somewhat smaller MEDTRONIC Model 3795 electrodes and are placed in a pattern above the right iliac muscle. Electrodes 154a through 154c are of the same type as electrodes 152a through 152c and are placed above the left quadriceps muscles. Finally, electrodes 155a through 155c are similar to electrodes 153a through 153c and are placed above the left iliac muscle. All electrodes are attached to the skin of the person by hypoallergenic tape or elastic bandages. Prior to application of the electrodes, the skin is cleaned and dried. An electrode gel, such as Tens electrode gel, also sold by Medtronic, Inc. is applied to the electrodes before they are placed upon the skin of the person.

In conventional exercycles it is common practice to provide means for monitoring the pulse rate of the operator. However, it has been found that the pulse rate of a paraplegic or quadriplegic person is not a reliable indicator of stress during electrically stimulated exercise. Thus, as shown schematically in FIG. 2, a blood pressure sensor 35 is attached to the arm of the person. Blood pressure sensor 35 may be a standard sphygmomanometer. Alternatively, an automatic device such as a Narco Bio-Systems PE-300 programmed electrosphygmomanometer may be utilized. During the course of a therapy procedure, as hereinafter described, the blood pressure is continually monitored, and the procedure is terminated if the pressure becomes abnormal.

Figure 3:
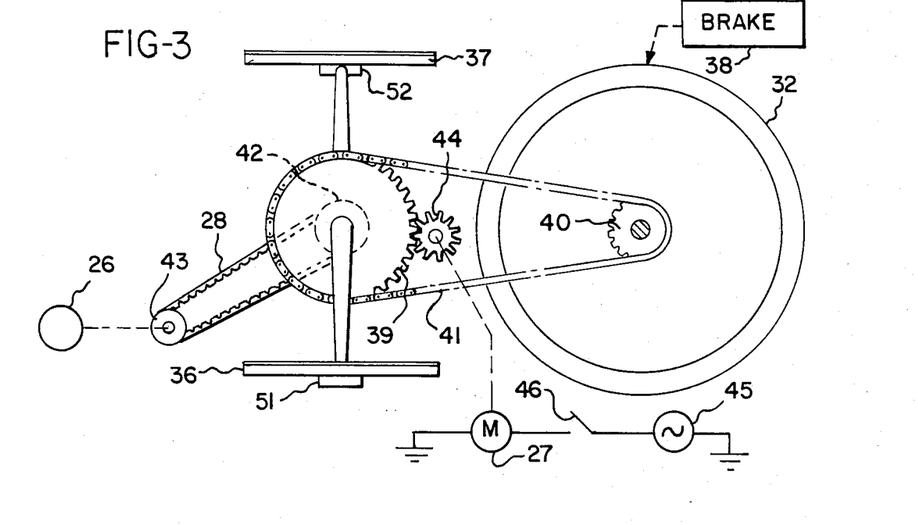
FIG. 3 is a schematic illustration of a chain drive for an exercycle to be operated by a paralyzed person.
Figure 4:
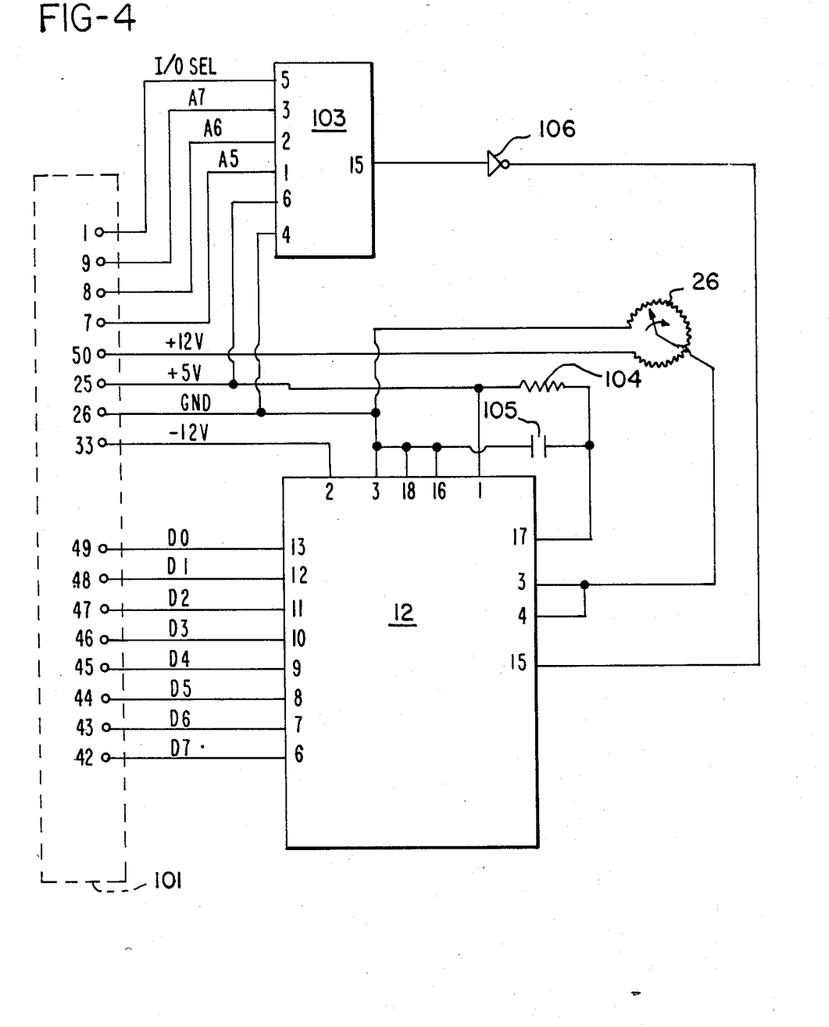
FIG. 4 is a schematic diagram of an analog to digital converter for use in the system of FIG. 1.

As the paralyzed person pedals the exercycle, pedals 51 and 52 rotate a conventional sprocket 39 for driving a drive chain 41. Drive chain 41 rotates a driven sprocket 40 for causing rotation of flywheel 32 against the braking action of brake 38. The support for pedals 51 and 52 also supports a drive gear 42 for driving a timing belt 28. When pedals 51 and 52 are rotated, timing belt 28 causes rotation of a driven gear 43 for operation of a position sensor 26. Position sensor 26 may be a simple rotary potentiometer connected to A/D converter 12 as illustrated in FIG. 4. Position sensor 26 is oriented so as to give an output angle indication of zero degrees for the top dead center position of right pedal 51 and right foot plate 36.

For the preferred embodiment, as described herein, a motor 27 is provided for initiating a pedaling motion, once the feet of the paralyzed person are in place against foot plates 36. Such rotation may be performed manually by an exercise assistant or by a motor 27. Motor 27 may be powered by a source of alternating current 45 and may drive a gear 44 mounted for engagement with sprocket 39. A switch 46 may be provided to activitate motor 27 until the legs of the paralyzed person are operating the exercycle. Switch 46 is closed a second time for temporary operation of motor 27 at the end of the exercise routine. This is done to prevent pooling of blood in the legs of the paralyzed person.

Figure 5:
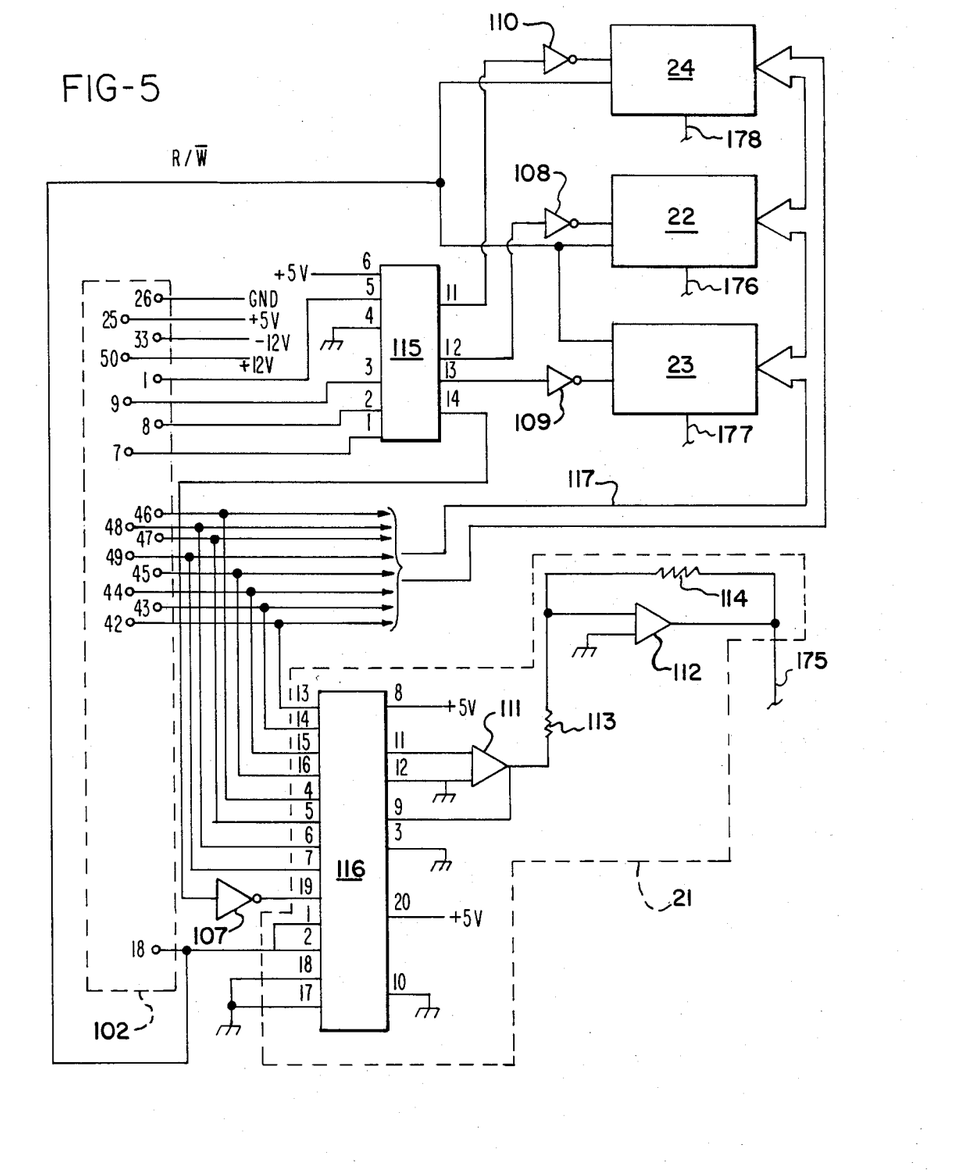
FIG. 5 is a schematic diagram showing electrical connections for digital to analog converters of the type shown in FIG. 1.
Figure 6:
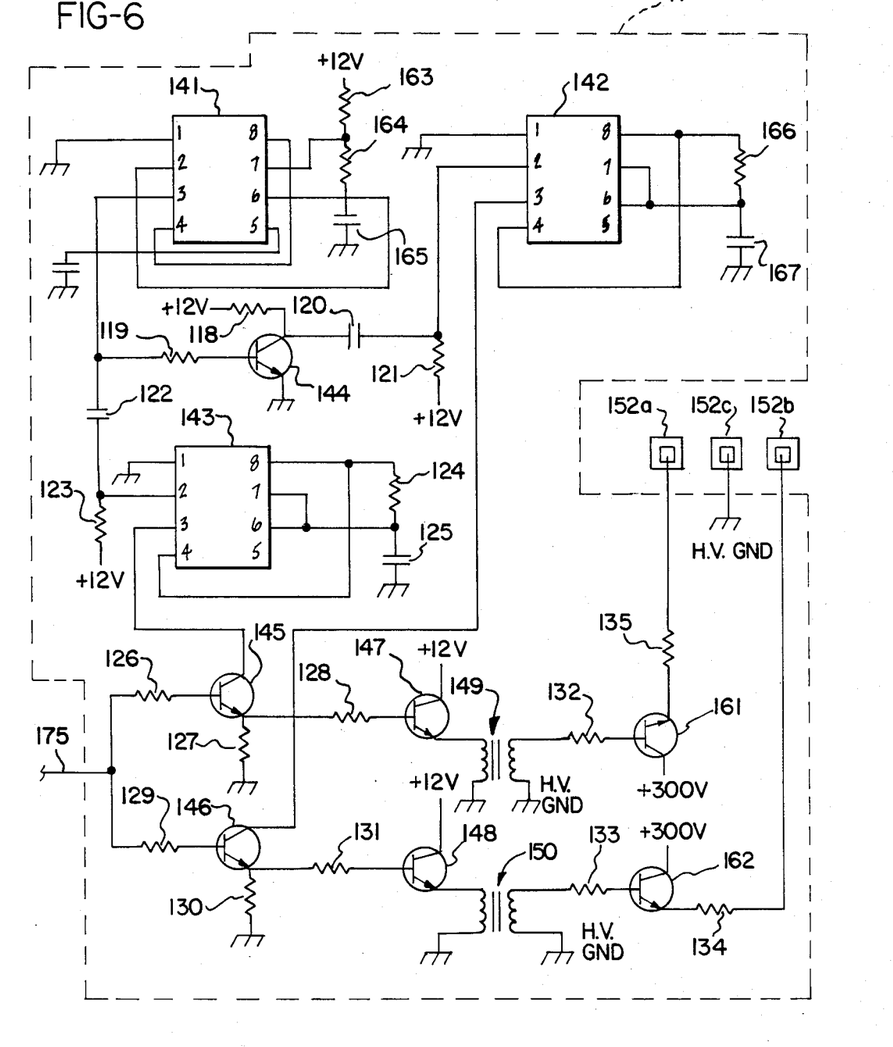
FIG. 6 is a schematic diagram of a muscle stimulation driver.

Electrical schematic diagrams for the exercising system are presented in FIGS. 4 through 6. Elements illustrated on those figures are identified in Table I. As noted above, computer 11 is an Apple II Plus computer. This computer is provided with slots into which peripheral equipment may be plugged. This invention utilizes slot numbers 5 and 7, as indicated by reference numerals 101 and 102, respectively. The slot connectors are illustrated by dotted lines in FIGS. 4 and 5. Computer 11 is programmed using a variation of the BASIC programming language known as APPLESOFT.

TABLE I

| Identification of Electrical Elements | |
|---|---|
| Reference Numeral | Identification |
| 101 | Connector for computer slot #7 |
| 102 | Connector for computer slot #5 |
| 103 | SN74LS138 (Texas Instruments) |
| 104 | 100K |
| 105 | 100 pf |
| 106 | 1/6 7406 |
| 107 | 1/6 7406 |
| 108 | 1/6 7406 |
| 109 | 1/6 7406 |
| 110 | 1/6 7406 |
| 111 | ½ LM1458 |
| 112 | ½ LM 1458 |
| 113 | 100K |
| 114 | 82K |
| 115 | SN74LS138 (Texas |

TABLE I-continued

| Identification of Electrical Elements | |
|---|---|
| Reference Numeral | Identification |
| | Instruments) |
| 116 | DAC0831 (National Semiconductor) |
| 118 | 10K |
| 119 | 10K |
| 120 | 0.001 μf |
| 121 | 22K |
| 122 | 0.001 μf |
| 123 | 22K |
| 124 | 10K |
| 125 | 0.1 μf |
| 126 | 470 Ω |
| 127 | 10K |
| 128 | 470 Ω |
| 129 | 470 Ω |
| 130 | 10K |
| 131 | 470 Ω |
| 132 | 1K |
| 133 | 1K |
| 134 | 100 Ω |
| 135 | 100 Ω |
| 141 | SE/NE 555 (Signetics) |
| 142 | SE/NE 555 (Signetics) |
| 143 | SE/NE 555 (Signetics) |
| 144 | 2N3904 |
| 145 | 2N3904 |
| 146 | 2N3904 |
| 147 | 2N3904 |
| 148 | 2N3904 |
| 161 | 2SC1308 |
| 162 | 2SC1308 |
| 163 | 100K |
| 164 | 100K |
| 165 | 0.1 μf |
| 166 | 10K |
| 167 | 0.1 μf |

A complete program listing is set forth in Table II. Paddle controllers 30 and 31 are provided by the computer manufacturer and are plugged into connectors provided therefor. Paddle controller 30 is plugged into the first paddle position (designated position 0 by the manufacturer), and paddle 31 is plugged into the second position (position 1). Paddle controllers 30 and 31 are operated manually as hereinafter described to produce stimulation signals having amplitudes for causing the legs of the paralyzed person to pedal the exercycle at a speed corresponding to some desired power output. Indicator 29 is monitored and paddle controllers 30 and 31 are adjusted accordingly.

As the legs pedal the exercycle, position sensor 26 provides a feedback indication of pedal position. The feedback signal, which is in analog form, is digitized by A/D converter 12. A digital representation of the paddle position is supplied to computer 11 via connections at slot number 7. Computer 11 reads the position angle indications, and generates four appropriately timed control signals for cooperatively stimulating the leg muscles of the paralyzed person. The amplitude of all four control signals is determined by the setting of paddle controllers 30 and 31, as stated above. The four control signals are supplied via slot number 5 to D/A converters 21 through 24. D/A converters 21 through 24 convert the control signals to analog format for use by stimulation drivers 47 through 50.

A/D converter 12 is mounted on a common board with a decoder/demultiplexer 103 and is interconnected therewith as illustrated in FIG. 4. The board including A/D converter 12 and IC 103 is connected into slot number 7 of computer 11 as illustrated. All operative connections are indicated by pin number. For ease of understanding, the output lines from connector 101 are identified as to function. Speciations for each of these outputs may be ascertained by consulting reference manuals provided by the computer manufacturer. At this point it is sufficient to note that A/D converter 12 is connected for supplying data along 8 data lines D-0 through D-7 to computer 11.

Connector 101 includes eight address lines for generation of an eight bit address. The three high order bits are applied to terminals 1, 2 and 3 of IC 101 for addressing A/D computer 12 at appropriate times during the computing cycle. As hereinafter noted in connection with the description of the program listing, A/D converter 12 must be addressed twice for generation of a single reading (in digital format) of the position of sensor 26.

FIG. 5 illustrates the interconnections for D/A converters 21 through 24. D/A converters 21 through 24 are connected to a common data bus 117 carrying data from slot number 5 of computer 11. A decoder/demultiplexer 115 is also connected into slot number 5 via connector 102 for selection of D/A converters as desired by computer 11. The four D/A converters have output lines 175 through 178, as indicated.

D/A converter 21 comprises an integrated circuit 116 and discrete components as illustrated in FIG. 5. D/A converters 22 through 24 are identical to D/A converter 21. Therefore, only D/A converter 21 is illustrated in detail in FIG. 5. D/A converter 21 is connected for stimulating the right quadriceps muscles through generation of an appropriate analog voltage (ranging between 0 and +12 volts) on line 175.

Analog control signals on line 175 are processed by stimulation driver 47 through use of circuitry which is illustrated in detail in FIG. 6. Stimulation drivers 48 through 50 are of identical contstruction and are not illustrated in detail. Stimulation driver 47 includes three integrated circuits 141, 142 and 143 of identical construction. These are timing circuits such as Signetics 555 timers. IC 141 is connected to operate as a 60 Hz free-running multivibrator. The output of IC 141 is applied via transistor 144 to input pins 2 of IC 142 and 143. IC 142 and 143 produce alternating 500 microsecond pulses each at a frequency of 60 Hz for application to the collector terminals of transistors 145 and 146. The pulse width is set by a appropriate selection of the resistance for resistors 166 and 124 and the compacitance of capacitors 167 and 125, as shown in the manufacturer's data sheets for integrated circuits 142 and 143. The phase between the pulses produced by integrated circuits 142 and 143 is set by appropriate selection of the resistance for resistors 163 and 164.

The analog control voltage generated on line 175 by D/A converter 21 is applied to the base terminals of transistors 145 and 146. Concomitantly, output pulses from pin 3 of IC 142 and pin 3 of IC 143 are applied to the collectors of transistors 146 and 145, respectively. As a result thereof, transistors 146 and 145 generate emitter currents across resistors 130 and 127 providing voltage profiles of the general shape illustrated in FIG. 7. These voltages are applied to the base terminals of transistors 148 and 147 for generating voltage pulses ranging between 0 and 12 volts across the primary windings of transformers 150 and 149.

Figure 7:
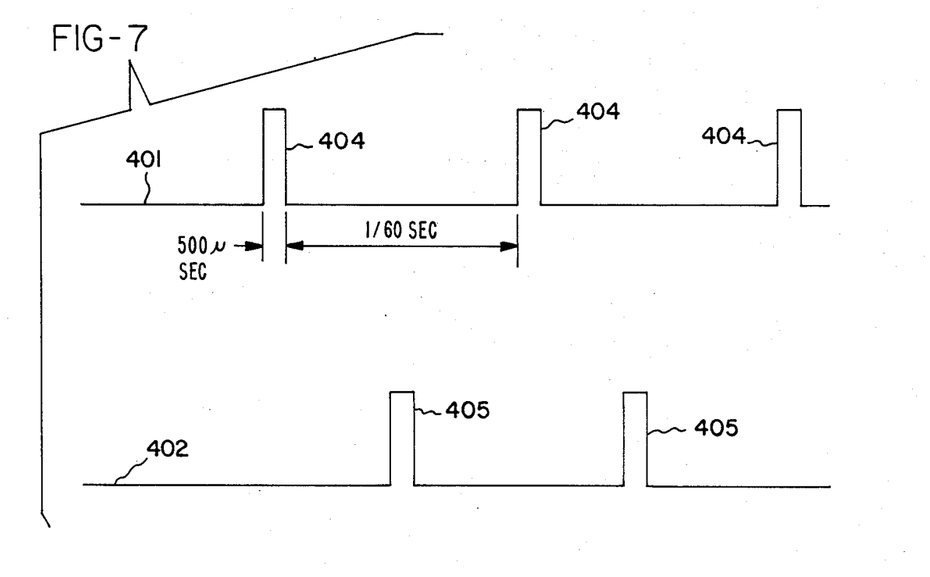
FIG. 7 is a schematic illustration of stimulation signals produced by the stimulation driver of FIG. 6.

The voltage pulses across the primary windings of transformers 150 and 149 produce low current, high voltage pulses ranging from 0 to 255 volts across the secondary windings of transformers 150 and 149. The secondary windings of transformers 150 and 149 have one side grounded to a high voltage ground which is different from the ground utilized for the primary windings thereof. The output pulses from the secondary windings are thereby RF isolated to maintain the safety of the paralyzed person.

Output voltages from transformers 150 and 149 are applied to the base terminals of transistors 162 and 161 respectively. Transistors 162 and 161 provide a current gain so as to have high current, high voltage and low duty cycle pulses available for application across terminal pairs 152a–152c and 152b–152c. The signals across the two terminal pairs are represented by signal lines 401 and 402, respectively, of FIG. 7. It will be noted that signals 401 and 402 comprise pulses 404 and 405, respectively. Pulses 404 and 405 are generated alternately at a frequency of 60 Hz each.

Alternating pulse signals as illustrated in FIG. 7 have been found to cause contraction of muscles which are ordinarily paralyzed. As noted above, the pulses have peak values at a level controlled by adjustment of paddle controllers 30, 31 (paddle controller 30 for stimulation driver 47) up to a maximum of 255 volts. Generally speaking, a voltage of about 255 volts produces recruitment of all motor units and results in maximum effort by the muscle. The maximum voltage applied at any point during a therapy procedure depends upon the state of exhaustion of the muscle. As the muscle tires, more stimulation voltage is required for production of the same effort, and this can be used as a guide for termination of stimulation.

As noted above, computer 11 directs the stimulation control signals to the appropriate stimulation drivers by controlling decoder/demultiplexer 115 to enable the correct ones of D/A converters 21 through 24. This operation is carried out under control of the computer program set forth in Table II.

Referring now to lines 14 through 17 of Table II, it will be seen that the program assigns the designations LQUAD, RQUAD, RIL and LIL to random access memory locations 50528, 50464, 50496 and 50560, respectively. The corresponding hexadecimal notations for these memory locations are C520, C540, C560 and C580. Those who are familiar with the programming of an Apple computer will understand that the two higher order digits of each of the above mentioned hexadecimal codes refer to a page of memory, while the two lower order digits refer to a memory location within that page. Each memory location is able to store a single eight-bit binary code representing the decimal numbers ranging between 0 and 255.

Whenever the program addresses any of the above mentioned memory locations, an eight-bit binary address representing the two lower order digits of the hexadecimal code appears at the address terminals of slot number 5 (connector 102). The three higher order bits of that address code, namely address bits A7, A6 and A5 appear at pin numbers 9, 8 and 7, respectively, of connector 102 for controlling the operation of decoder/demultiplexer 115.

When the system desires to direct a stimulation command to a particular muscle, the computer executes a "POKE" instruction, such as the instruction appearing at program line 600. That instruction tells the computer to load a value H into the location RQUAD (50464 decimal or C520 hexadecimal). The value H is obtained at program step 405 by reading the setting of paddle 0 (paddle controller 30). When the instruction at line number 600 is executed, an eight-bit binary code representing the setting of paddle 0 appears at pin numbers 42 through 46 of connector 102 for transmission along data bus 117 to each of D/A converters 21 through 24. Concomitantly therewith a three-bit binary code representing the three high order bits of the four-bit binary code corresponding to a hexadecimal 2 (i.e. 001) appears at pins 9, 8 and 7 of connector 102 for selection of D/A converter 21 by decoder/demultiplexer 115. As a result, a binary code representing the setting of paddle controller 30 is sent to stimulation driver 47 for stimulating the right quadriceps muscles.

The left quadriceps muscles are similarly stimulated by poking eight-bit binary numbers into memory location 50528. In like manner, the right iliac and left iliac muscles are stimulated through poking of memory locations 50496 and 50560.

The program reserves memory location 50944 for storage of pedal position information from pedal sensor 26. Reading of pedal position information into that storage location is accomplished at line number 400 by executing a pair of "PEEK" instructions. Both instructions check the value stored at memory location 50944 and set the variable U equal to that value. Two executions of the instruction cause a sequence whereby A/D converter 12 reads the position of sensor 26 and transmit a digital representation of that position to connector 101 for storage in memory location 50944.

After the pedal position has been read, then the computer makes a check to determine the quadrant position of the pedal. This check is made at line numbers 410 through 440. If the variable U (as indicated by memory location 50944) has a value between 15 and 74, then the right pedal is deemed to be in the first quadrant, as defined above, and the program branches to step No. 600 whereupon the right quadriceps and left iliac muscles are stimulated. If the variable U has a value between 74 and 128, then the right pedal is deemed to be in the second quadrant, and program branches to step No. 700 for stimulation only of the left iliac muscle. If the variable U has a value between 132 and 196, then the program branches to line number 800 for stimulating the left quadriceps and right iliac muscles. Finally, if the variable U has a value between 191 and 255, then the program branches to line number 900 for stimulation only of the right iliac muscle.

A physical therapy procedure utilizing the above hardware and software will now be described. However, it should be noted at this point that a paralyzed person should not be subjected to such a procedure unless he or she is in good physical condition therefor. Thus the procedure should be preceded by a physical examination. Moreover, it is desirable that the strength of the legs be built up somewhat before commencing the procedure. Such a build up may be accomplished using a leg trainer of the type described in copending application Ser. No. 417,935. Exercise should continue on such a leg trainer until the legs are each able to lift a weight of ten pounds.

A physical therapy procedure in accordance with this invention is commenced by applying electrodes to the subject in a pattern as shown in FIG. 2. Other electrodes (not illustrated) may be applied to the chest for production of electrocardiograms as desired throughout the procedure. Thereafter, the subject is seated on the exercycle and the shoulder straps and seatbelt are fastened. Then electrical connections are made to the stimulation electrodes and leg braces 19, 19 are secured to the legs. Blood pressure sensor 35 may be attached at this time, and tension control 33 is adjusted to a setting of 0 kiloponds, so that movement of the legs will be impeded a very low, nominal resistance.

The next step in the procedure is the commencement of passive pedaling. Passive pedaling is carried out either manually or through use of drive motor 27 and continues until a speed of approximately 10 kilometers per hour is reached.

After a speed of about 10 kilometers per hour has been achieved, paddle 0 (paddle controller 30) is turned on to begin stimulation of the quadriceps muscles. The stimulation is adjusted to a level such that the quadriceps muscles are able to sustain the speed of 10 kilometers per hour. Thereafter, paddle 1 (paddle controller 31) is turned up to begin stimulation of the iliac muscles. As paddle 1 is turned upwardly, an increase of pedaling speed will be noted.

Upward adjustment of the paddle is continued until the indicated exercycle speed is about 15 kilometers per hour. Thereafter, paddle 0 is adjusted upwardly to achieve an indicated speed of about 17 kilometers per hour at the 0 kilapond tension setting.

Tension control 33 is then adjusted upwardly to achieve a desired power output level for training the individual. Based upon experimental data from previous procedures for the same person, the tension control is set at that level which will enable about 15 to 30 minutes of exercise. As the endurance of the person increases, the tension level likewise is increased. A typical tension setting for a person who is beginning training on the systems is about 0.25 kiloponds.

As the tension setting is moved upwardly from the initial zero value, the setting of paddle 0 is increased to increase the stimulation voltage to the quadriceps and maintain the pedaling speed at about 17 kilometers per hour. Thereafter, as the therapy procedure continues and the muscles begin to tire, a decrease in the pedaling speed will be noted. This is prevented by gradual upward adjustment of paddle 0.

Upward adjustment of the stimulation voltage applied to the quadriceps muscles is continued until a point is reached where a further increase in voltage does not increase pedaling speed. The exercise is continued at that setting until the indicated speed decreases to about 12 kilometers per hour. At this point the stimulation is terminated by turning off the computer. Then passive pedaling is again undertaken so as to prevent venous pooling. Passive pedaling is continued for about two minutes and thereafter is terminated.

As noted above, the blood pressure of the subject is monitored throughout the course of the therapy procedure. The blood pressure is also measured prior to commencement of the procedure, while the subject is resting. The procedure is terminated in any case if the pressure during exercise becomes as great as twice the resting pressure. Quite frequently paraplegic and quadriplegic persons have a normal blood pressure which is lower than the pressure customarily observed for non-handicapped persons. Therefore, as a general precautionary guide, the procedure is terminated if the systolic pressure exceeds 180 mm Hg or if the diasolic pressure exceeds 140 mm Hg. The procedure is also terminated if abnormal electrocardiograms are recorded.

While the method herein described and the form of apparatus for carrying this method into effect constitute a preferred embodiment of this invention, it is to be understood that the invention is not limited to this precise method and form of apparatus, and that changes may be made in either without departing from the scope of the invention which is defined in the appended claims.

TABLE II

| | Program Listing |
|---|---|
| 1 | FOR X = 0 TO 3 |
| 2 | A = 50464 + X * 32: POKE A,O: PRINT A |
| 3 | NEXT X |
| 10 | PRINT "TYPE GO TO START" |
| 14 | LQUAD = 50528 |
| 15 | RQUAD = 50464 |
| 16 | RIL = 50496 |
| 17 | LIL = 50560 |
| 19 | REM |
| 20 | INPUT A$ |
| 30 | IF A$ = "GO" THEN GOTO 50 |
| 40 | GOTO 10 |
| 50 | FLASH : PRINT "SYSTEM ACTIVE": NORMAL |
| 300 | REM MAKE BIKE MOVE |
| 400 | U = PEEK (50944):U = PEEK (50944) |
| 405 | H = PDL (0):J = PDL (1) |
| 410 | IF U > 15 AND U < 74 THEN GOTO 600 |
| 420 | IF U > 74 AND U < 128 THEN GOTO 700 |
| 430 | IF U > 132 AND U < 196 THEN GOTO 800 |
| 440 | IF U > 191 AND U < 255 THEN GOTO 900 |
| 445 | POKE RQUAD,O: POKE LQUAD,: POKE RIL,O: POKE LIL,0 |
| 460 | GOTO 400 |
| 600 | POKE RQUAD,H |
| 610 | POKE LIL,J |
| 620 | POKE LQUAD,O: POKE RIL,O |
| 630 | GOTO 400 |
| 700 | POKE RQUAD,O |
| 705 | POKE LIL,J |
| 720 | POKE LQUAD,O: POKE RIL,O |
| 740 | GOTO 400 |
| 800 | POKE LQUAD,H |
| 810 | POKE RIL,J |
| 820 | POKE RQUAD,O: POKE LIL,O |
| 830 | GOTO 400 |
| 900 | POKE RQUAD,O: POKE LIL,O: POKE LQUAD,O |
| 910 | POKE RIL,J |
| 940 | GOTO 400 |
| 1040 | END |

What is claimed is:

1. A treatment system for a paralyzed person comprising:
    a pair of oppositely disposed pedals mounted for rotation about an axis,
    load means responsive to rotation of said pedals for generating a rotation resisting torque,
    sensing means for sensing the position of said pedals,
    computing means responsive to said sensing means for generating first, second, third and fourth control signals,
    stimulation means responsive to said first, second, third and fourth control signals for cooperatively stimulating the right quadriceps, left quadriceps, right iliac and left iliac muscles respectively of said person to cause rotation of said pedals against said resisting torque, and
    amplitude control means connected to said computing means for adjusting the amplitude of said control signals.

2. A system according to claim 1 and further comprising power indicating means for indicating the power input to said pedals.

3. A system according to claim 1 and further comprising motive means for powering rotation of said pedals against said resisting torque during initiation and termination of a therapy procedure for said person.

4. A system according to claim 1 and further comprising means for measuring the blood pressure of said person during the operation of said system.

5. A system according to claim 1 wherein said stimulation means comprises twelve transcutaneous stimulation electrodes connected in groups of three for activation by said four control signals; each said control signal causing generation of voltage pulses across alternate pairs of electrodes within its associated three-electrode group.

6. A system according to claim 5 wherein said stimulation means comprises means for generating said pulses across each said electrode pair at a frequency of about 60 Hz and with each said pulse having a duration of about 500 microseconds.

7. A system according to claim 1 wherein said amplitude control means comprises first gain control means for adjusting the amplitude of said first and second control signals and second gain control means for adjusting the amplitude of said third and fourth control signals.

8. A system according to claim 7 wherein said first gain control means and second gain control means are manually adjustable.

9. A treatment system for paralyzed persons comprising:
a pair of oppositely disposed pedals mounted for rotation about a common axis,
means for maintaining the feet of said persons in engagement with said pedals,
load means responsive to rotation of said pedals for generating a rotation resisting torque,
sensor means for sensing the position of said pedals,
computing means responsive to said sensing means for generating first, second, third and fourth control signals,
stimulation means responsive to said first, second, third and fourth control signals for stimulating the iliac muscles and quadriceps muscles of said persons to cause rotation of said pedals against said resisting torque,
first gain control means connected to said computing means for adjusting the amplitude of said first and second control signals,
second gain control means connected to said computing means for adjusting the amplitude of said third and fourth control signals, and
motive means for powering rotation of said pedals against said resisting torque during initiation and termination of a therapy procedure for said person.

10. A system according to claim 9 wherein said stimulation means comprises twelve transcutaneous stimulation electrodes connected in groups of three for activation by said four control signals; each said control signal causing generation of voltage pulses across alternate pairs of electrodes within its associated three-electrode group.

11. Physical therapy method for a person having paralyzed legs comprising the steps of:
applying electrical stimulation signals to the iliac and quadriceps muscles of said person to produce coordinated movement of said legs,
impeding the movement of said legs,
measuring the power output from said legs, and
adjusting said stimulation signals to maintain said power output at a predetermined level.

12. Method according to claim 11 wherein said coordinated movement is a pedaling movement.

13. Method according to claim 12 wherein an exercycle is used for impeding the movement of said legs.

14. Method according to claim 13 wherein said power output is measured indirectly by measuring the operating speed of said exercycle.

15. Method according to claim 13 and further comprising the steps of assisting said person by independently operating said exercycle prior to and following application of stimulation signals as aforesaid.

16. Method according to claim 11 and further comprising the step of terminating the application of stimulation signals when the response of said muscles to the application of said stimulation signals decreases to such a degree as to indicate a state of exhaustion.

17. Method according to claim 11 and further comprising the steps of measuring the systolic and diastolic blood pressures of said person and terminating application of stimulation signals as aforesaid when said systolic blood pressure beomes greater than about 180 mm Hg or when said diastolic blood pressure becomes greater than about 140 mm Hg.

18. Method according to claim 11 and further comprising the step of:
applying at least three transcutaneous stimulation electrodes over each muscle group being stimulated; said electrical stimulation signals comprising alternately pulsed signal components and being applied across alternate pairs of said electrodes.

19. Physical therapy method for a person having paralyzed legs comprising the steps of:
applying transcutaneous stimulation electrodes over the right quadriceps, left quadriceps, right iliac and left iliac muscles of said person,
applying first, second, third and fourth electrical stimulation signals to those of said electrodes which are placed respectively over said right quadriceps, left quadriceps, right iliac and left iliac muscles to create a pedaling moition by said legs,
impeding the movement of said legs by a nominal low resistance,
measuring the power output from said legs,
measuring the pedaling position angle achieved by said legs,
adjusting the amplitude of said first and second stimulation signals to maintain said power output at a predetermined level, and
adjusting the timing of said stimulation signals in accordance with said position angle to coordinate said pedaling motion.

20. Method according to claim 19 wherein only said first and fourth stimulation signals are turned on during a first quadrant of said pedaling motion, only said fourth stimulation signal is turned on during a second quadrant of said pedaling motion, only said second and third stimulation signals are turned on during a third quadrant of said pedaling motion, and only said third stimulation signal is turned on during a fourth quadrant of said pedaling motion; said first, second, third and fourth quadrants following each other in sequence.

21. Method according to claim 20 and further comprising the step of assisting said person by independently powering said pedaling motion prior to activation of any of said stimulation signals.

22. Method according to claim 21 wherein activation of said stimulation signals is commenced with all of said stimulation signals at a low, non-functional level followed by the steps of:

increasing the amplitude of said first and second stimulation signals to a first functioning level at which said legs are self-pedaling at a first predetermined speed, thereafter increasing the amplitude of said third and fourth stimulation signals until said legs are self-pedaling at a second predetermined speed greater than said first predetermined speed, thereafter increasing the amplitude of said first and second stimulation signals to a second functioning level at which said legs are self-pedaling against said resistance at a third predetermined speed greater than said second predetermined speed, and thereafter increasing said resistance and the amplitude of said first and second stimulation signals to produce a predetermined power output at said third speed.

23. Method according to claim 22 and further comprising the step of turning off all of said stimulation signals when said legs are not able to maintain a fourth predetermined speed lower than said third predetermined speed during application of said first and second stimulation signals at a predetermined third functioning level greater than said second functioning level.

24. Method according to claim 23 and further comprising the step of independently powering said pedaling motion for at least about two minutes following termination of said stimulation signals.

25. Method according to claim 24 and further comprising the step of measuring the systolic and diastolic blood pressures of said person.

26. Method according to claim 25 wherein each of said stimulation signals comprises a pair of pulsed signal components; each said component comprising pulses generated at a frequency of about 60 Hz.

27. Method according to claim 26 wherein said pulses have a duration of about 500 microseconds.

28. Method according to claim 27 wherein three of said electrodes are placed over each of said muscles.

29. Method according to claim 28 wherein said signal components are applied across said electrodes in different pairs.

30. Method according to claim 24 wherein said stimulation signals are applied for a period of time ranging between about 15 and 30 minutes.

31. Apparatus for treating a paraylzed person comprising;
stimulation means for stimulating the muscles of said person to produce cyclic coordinated movement of both legs,
means for impeding the movement of said legs,
means for indicating the power output from said legs, and
means for adjusting said stimulation means to maintain said power output at a predetermined level.

32. Apparatus according to claim 31 wherein said stimulation means comprises means for separate stimulation of the quadriceps muscles and iliac muscles of said person and said last named means comprises means for independent adjustment of said separate stimulation.

33. A treatment system for a paralyzed person comprising:
a pair of oppositely disposed pedals mounted for rotation about an axis,
load means for generating a torque to resist rotation of said pedals,
sensing means for sensing the position of said pedals and generating a corresponding sensing signal,
computing means for generating a plurality of stimulation control signals under timing control of said sensing signal, and
stimulation means responsive to said stimulation control signals for stimulating the legs of a paralyzed person to engage in cooperative pedalling motion against said pedals.

34. Apparatus according to claim 33 and further comprising means for manually adjusting the amplitude of said stimulation control signals.

35. Apparatus according to claim 33 and further comprising a seat for said paralyzed person, means for maintaining the feet of said person in engagement with said pedals and a pair of braces for supporting said legs.

* * * * *